United States Patent [19]

Tarancon

[11] 4,249,917
[45] Feb. 10, 1981

[54] STERILIZATION GAS SEPARATION PROCESS

[75] Inventor: Gregorio Tarancon, Woodbridge, N.J.

[73] Assignee: Union Carbide Corporation, New York, N.Y.

[21] Appl. No.: 96,406

[22] Filed: Nov. 21, 1979

[51] Int. Cl.³ .............................................. B01D 53/14
[52] U.S. Cl. ............................................ 55/48; 55/71; 55/89; 570/180
[58] Field of Search .................. 55/31, 32, 48, 71, 89; 260/652 P, 653, 704, 705, 708

[56] References Cited

U.S. PATENT DOCUMENTS

| | | | |
|---|---|---|---|
| 2,622,088 | 12/1952 | Thomas | 55/89 X |
| 2,775,600 | 12/1956 | Maslan | 260/708 X |
| 3,174,262 | 3/1965 | Lutz | 55/48 |
| 3,217,466 | 11/1965 | Bogart | 55/48 X |
| 3,617,209 | 11/1971 | Massonne et al. | 55/48 |
| 3,856,484 | 12/1974 | Cocuzza et al. | 55/48 |
| 4,028,070 | 6/1977 | Uchii et al. | 55/48 |

FOREIGN PATENT DOCUMENTS 1179106   1/1970   United Kingdom .................. 55/71

Primary Examiner—Robert H. Spitzer
Attorney, Agent, or Firm—Saul R. Bresch

[57] ABSTRACT

A process for the separation of a second mixture consisting essentially of ethylene oxide and dichlorodifluoromethane from a first mixture comprising ethylene oxide, dichlorodifluoromethane, and air comprising passing the first mixture through two zones connected in series, in a closed system, according to the following steps:

(a) passing the first mixture, in gaseous form, into an absorption zone and contacting said first mixture therein counter-currently with an organic liquid solvent, which has a boiling point of at least about 120° C. and is capable of absorbing ethylene oxide and dichlorodifluoromethane under process conditions, at a pressure of about 80 psia to about 450 psia and a temperature of about minus 12° C. to about 24° C., the solvent being present in a sufficient amount to absorb essentially all of the ethylene oxide and dichlorodifluoromethane whereby liquid bottoms are formed, and the air, in gaseous form, passes overhead;

(b) passing the bottoms from step (a) into a desorption zone wherein the pressure is in the range of about 5 psia to about 25 psia, and the temperature is in the range of about minus 12° C. to about 24° C. at the top of the zone and in the range of about 40° C. to about 120° C. at the bottom of the zone with a temperature gradient in between, in such a manner that the ethylene oxide and dichlorodifluoromethane are vaporized forming a gaseous overhead and the solvent forms liquid bottoms; and (c) recovering the overhead from step (b).

3 Claims, 1 Drawing Figure

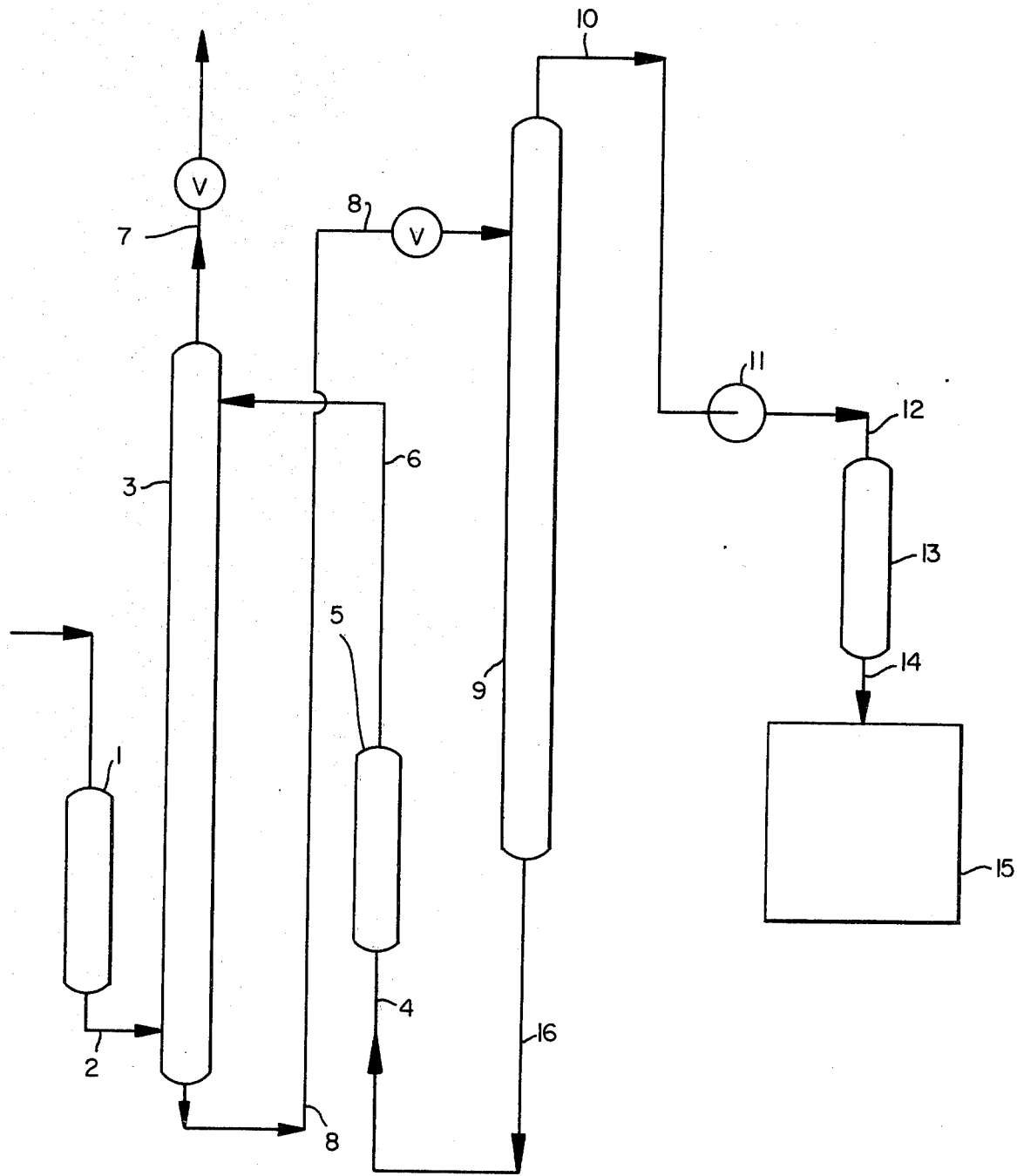

STERILIZATION GAS SEPARATION PROCESS

FIELD OF THE INVENTION

This invention relates to a process for the separation of a sterilization gas from impurities acquired during the sterilization process and, more particularly, to a process for the separation and recovery of a mixture of ethylene oxide and dichlorodifluoromethane from air.

DESCRIPTION OF THE PRIOR ART

Industrial sterilizers commonly utilize a gaseous mixture of ethylene oxide and dichlorodifluoromethane in proportions which will inhibit the explosive qualities of the ethylene oxide. In the past, the post-sterilization mixture, which had increased its volume by about one hundred percent through the accumulation of air and water vapor in the sterilization procedure, was merely vented into the atmosphere. This means of disposing of mixtures of this type is no longer environmentally desirable. Further, rising costs have stimulated industry to search for techniques for recovering the ethylene oxide/dichlorodifluoromethane mixture in its original pure state, i.e. prior to the use of the mixture in the sterilizer. While it was recognized that the water vapor could be easily removed by known procedures and that some of the air could be removed by condensation from a saturated mixture, the separation of the remaining air from the ethylene oxide/dichlorodifluoromethane mixture was considered the major stumbling block to a commercially practical recovery.

SUMMARY OF THE INVENTION

An object of this invention, therefore, is to provide a process for the separation of ethylene oxide and dichlorodifluoromethane from air.

Other objects and advantages will become apparent hereinafter.

According to the invention such a process has been discovered for the separation of a mixture consisting essentially of ethylene oxide and dichlorodifluoromethane (second mixture) from air including passing a first mixture comprised of ethylene oxide, dichlorodifluoromethane, and air through two zones connected in series, in a closed system, according to the following steps:

(a) passing the first mixture, in gaseous form, into an absorption zone and contacting said first mixture therein counter-currently with an organic liquid solvent, which has a boiling point of at least about 120° C. and is capable of absorbing ethylene oxide and dichlorodifluoromethane under process conditions, at a pressure of about 80 psia to about 450 psia and a temperature of about minus 12° C. to about 24° C., the solvent being present in sufficient amount to absorb essentially all of the ethylene oxide and dichlorodifluoromethane whereby liquid bottoms are formed, and the air, in gaseous form, passes overhead;

(b) passing the bottoms from step (a) into a desorption zone wherein the pressure is in the range of about 5 psia to about 25 psia, and the temperature is in the range of about minus 12° C. to about 24° C. at the top of the zone and in the range of about 40° C. to about 120° C. at the bottom of the zone with a temperature gradient in between, in such a manner that the ethylene oxide and dichlorodifluoromethane are vaporized forming a gaseous overhead and the solvent forms liquid bottoms; and (c) recovering the overhead from step (b).

BRIEF DESCRIPTION OF THE DRAWING

The sole FIGURE of the drawing is a schematic flow diagram of an illustrative embodiment of the invention.

DESCRIPTION OF THE PREFERRED EMBODIMENT

The process of the invention utilizes two zones, an absorption zone and a desorption zone, connected in series. Although the process can be run as a continuous, semi-continuous, or batch process, it is preferably run in the continuous mode. The apparatus, which includes packed columns, heat exchangers, compressors, vacuum and liquid pumps, control and relief valves, storage tanks, piping, etc. is constructed in a conventional manner of conventional materials adequate to achieve and contain the various process temperatures, pressures, and chemicals. The system can be fabricated using such materials of construction as carbon steel, stainless steel, or brass. Sizing of the system takes into consideration capacities and economics while selection of materials is based on economics, longevity, and availability.

The process is carried out in a "closed system," i.e., it is air tight so that essentially no air or water vapor can get into the system to contaminate the product. The closed system is achieved by conventional sealing techniques. A dry, commercially pure solvent is used initially and then the process solvent is reused thus avoiding a possible source of contamination.

The packing in the columns is equivalent to about 3 to 15 theoretical mass transfer units, and pall rings, raschig rings, semi-rings, flexirings, or steel wool, made of carbon steel, stainless steel, copper, nickel/copper alloy, or nickel or their conventional equivalents can be used for packing the columns, the objective of the packing being to achieve a high level of gas/liquid contact in the absorption zone and a high level of desorption in the desorption zone.

The gas from the sterilizer is a mixture comprising about 1 to about 30 percent by volume ethylene oxide; about 4 to about 70 percent by volume dichlorodifluoromethane; about 1 to about 5 percent by volume water vapor; and about 1 to about 90 percent by volume air, percent by volume being based on the total volume of the mixture.

Instead of volume percentages, the amount of water may be described in terms of saturation at a particular temperature since in a typical case, the gas coming from the sterilizer is saturated, is at 27° C., and at atmospheric pressure.

The system in which the process of the invention is conducted is usually connected directly to the outlet stream of the sterilizer or to a storage tank. The impure gas mixture coming from the sterilizer or storage tank is usually at a temperature in the range of about 20° C. to about 60° C.

The first two procedures that are performed with regard to the outlet stream of the sterilizer are considered to be conventional. One procedure removes the water and the other serves to condense a portion of the ethylene oxide/dichlorodifluoromethane, an economic measure to reduce the size of the absorption and desorption columns and the amount of solvent utilized in subject process. While there are various ways to achieve the objectives of water removal and partial condensation, a preferred mode can be carried out as follows:

The impure mixture, i.e., ethylene oxide, dichlorodifluoromethane, water vapor, and air, is fed into a heat exchanger where the temperature is brought to the operating temperature of an absorption column (or tower), which is in the range of about minus 12° C. to about 24° C. and is preferably about 0° C. to about 5° C. The mixture then passes into the bottom of the column, which can be described as a vertical column packed with the same kind of commercial packing which was mentioned previously. The diameter of the column is preferably at least eight times the equivalent diameter of the packing, i.e. each piece of packing. The material of construction of the column is preferably carbon steel or any other comparable material. The liquid solvent is fed at the top evenly through a liquid distributor which is located above the packing and below the reflux condenser. The gas mixture which is going to be treated is injected into the opening at the bottom of the column but below the packing support plate. The clearance between the inlet of the gas mixture and the packing support plate is no greater than the radius of the tower. A conventional water miscible solvent, e.g., ethylene glycol, is fed into the top of the absorption column and passes counter-current to the vaporous mixture rising upwards through the column. Mass transfer (absorption) takes place in the packing, and the mixture, less essentially all of its water vapor content, passes out of the top of the column, and the ethylene glycol, now a liquid mixture containing the absorbed water from the gas mixture, flows out of the bottom of the column. The pressure in the column is in the range of about 5 to about 25 pounds per square inch absolute (psia) and is preferably about 18 psia to about 20 psia. The wet ethylene glycol passes through two heat exchangers in series where its temperature is raised to about 0° C. to about 120° C. and then the glycol passes into the top of a desorption column, which can be described as a typical vertical column, the type of packing and the method of packing the column as well as the material of construction of the column being the same as the previously described absorption column. This column has a reboiler at the bottom. The liquid mixture is fed into the column through a liquid distributor which is located at the top of column and above the packing. The operating conditions of the desorption column include a temperature in the range of about 70° C. to about 120° C. and preferably about 95° C. to about 110° C. and a pressure in the range of about 1 psia to about 10 psia and preferably about 3 psia to about 6 psia. The water is desorbed as steam, which is condensed in a condenser. The reduced pressure in the column is maintained by means of a vacuum pump and the water resulting from the condensation is discarded. The essentially dry glycol flows out of the bottom of the column, is pumped into a heat exchanger where it is cooled, and then recycled or recovered for reuse.

The dry gas mixture from the absorption column meanwhile passes into a compressor where it is compressed to a pressure in the range of about 80 psia to about 450 psia and preferably about 120 psia to about 360 psia.

When the concentration of the ethylene oxide/dichlorodifluoromethane mixture in air is above its saturation point, the amount of ethylene oxide/$CCl_2F_2$ above saturation can be removed by condensation. A typical saturation point is about 27 percent at 195 psia and ambient temperature. As a practical matter, however, the ethylene oxide, $CCl_2F_2$, air mixture is only sent to the condenser when the ethylene oxide/$CCl_2F_2$ is present in amounts of at least about 15 percent above saturation. Otherwise, the cost of condensation does not justify the recovery. If condensation is desired, the compressed mixture is cooled and sent to the condenser and the condensate, essentially free of air, passes to a storage tank.

Referring to the drawing:

The remaining gas mixture, which contains ethylene oxide, dichlorodifluoromethane, and air is first taken through heat exchanger 1 where it is cooled to a temperature in the range of about 12° C. to about 24° C. The mixture then passes through line 2 into the bottom of column 3, which can be described as a typical vertical tower or column, the type of packing and the method of packing the column as well as the material of construction of the column being the same as the absorption column previously described. The solvent is fed into column 3 through a distributor which is located above the packing; and the gas mixture is injected under the packing support plate. Any column having similar characteristics can be used here. The mixture meets the solvent in column 3 in a counter-current mode. This solvent is coming from line 4 through heat exchanger 5 where it is cooled to a temperature in the range of about minus 12° C. to about 24° C., and preferably about 0° C. to about 5° C., and then through line 6 into the top of column 3. The contact of the gas mixture with sufficient solvent in column 3 under a pressure in the range of about 80 psia to about 450 psia, and preferably about 120 psia to about 360 psia, and at a temperature in the range of about minus 12° C. to about 24° C., and preferably about minus 5° C. to about 5° C., causes essentially all of the ethylene oxide and dichlorodifluoromethane to be absorbed into the solvent, and air, essentially free of the two components, passes out of the top of column 3 through vent line 7 into the atmosphere. The solvent passing out of the bottom of column 3 through line 8 is rich in ethylene oxide and dichlorodifluoromethane and this liquid is fed into the top of column 9, which can also be described as a typical vertical column, the type of packing and the method of packing the column as well as the material of construction of the column being the same as in the absorption column. In comparison with the absorption column, this column has an extra feature, i.e., a reboiler (not shown) which is located at the bottom right below the packing support plate. The liquid mixture is fed into the column through a distributor which is located above the packing and below a reflux condenser. Any column having similar characteristics can be used here. The liquid is depressurized in column 9 to a pressure in the range of about 5 psia to about 25 psia, and preferably about 15 psia to about 20 psia, and essentially all of the dichlorodifluoromethane and ethylene oxide is vaporized and desorbed from the solvent. To aid in the desorption, the temperature at the top of column 9 is in the range of about minus 12° C. to about 24° C. and preferably about minus 5° C. to about 5° C. and the temperature at the bottom of column 9 is in the range of about 40° C. to about 120° C. and preferably about 95° C. to about 105° C. It is understood that there is a temperature gradient running from top to bottom. Column 9 preferably has a small gas inlet port immediately below the packing support plate where some of the purified air passing out of column 3 through line 7 can be fed into column 9 to aid in a more complete desorption of the ethylene oxide/dichlorodifluoromethane mixture from the solvent (the port and the connection from line 7 are not shown). The gas mixture then passes through line 10 and is pumped by compressor 11 through line 12, heat exchanger 13 (where it becomes a liquid) and line 14 into storage tank 15. The mixture in storage tank 15 is maintained as a liquid at a pressure in the range of about 40 psia to about 120 psia. The solvent meanwhile passes from column 9 as bottoms through line 16, line 4, heat exchanger 5, and line 6 to column 3. A preferred system has heat exchangers located in the top and at the bottom of column 9. The process fluids (liquid or gaseous) are used to provide heating or cooling in the heat exchangers wherever possible, but external fluids compatible with the system and at useful temperatures and purities can be introduced as needed. There are also several control valves located in appropriate places along the various lines connecting the pieces of apparatus used in the system.

Those skilled in the art will recognize that the solvents, which can be used in subject process, are conventional. As noted, they are organic liquids having boiling points of at least about 120° C. and are capable, in sufficient amount, of absorbing essentially all of the ethylene oxide and dichlorodifluoromethane in the system under process conditions. It will be understood that in order to take advantage of the absorption capacity of the solvent, an optimum ratio of the mixture of ethylene oxide and dichlorodifluoromethane (solute) to solvent will have to be used. The ratio of solute to solvent can be about 0.01 to about 1 part by weight of solute to each part by weight of solvent. The higher the pressure the lower the amount of solvent required, and the lower the pressure the greater the amount of solvent required, to absorb the solute, i.e., the ethylene oxide/dichlorodifluoromethane mixture. Also, the lower the temperature, the lower the amount of solvent required and the higher the temperature, the greater amount of solvent is required to absorb the solute. There is no upper limit to the amount of solvent that can be used, except the limit of practicality. On the other hand, at about 450 psia and minus 12° C., the use of much less than about one part by weight of solvent per part by weight of solute is risky because of the possibility of explosion through the decomposition of ethylene oxide. The solvents will be selected in accordance with their ability to absorb the greatest amount of mixture. Generally, the solvents contemplated are compounds containing carbon, hydrogen, and oxygen present as alkyl and alkylene radicals, predominantly those with one to five carbon atoms, hydroxyl groups, and ether linkages. They preferably have a much lower vapor pressure than the ethylene oxide/dichlorodifluoromethane mixture, e.g., less than about 10 or even 5 millimeters of mercury; a decomposition temperature much higher than process temperatures; a viscosity of less than about 150 centipoises; and a low surface tension to prevent foaming. Examples of solvents, which can be used in subject process, and can also be used for water removal, are diethylene glycol monobutyl ether, n-butyl alcohol, diethylene glycol monobutyl ether acetate, ethoxytriglycol, diethylene glycol monohexyl ether, and ethylene glycol monohexyl ether. Examples of solvents, which can be used in subject process, but not for water removal, are kerosene and n-decane. Examples of solvents which can be used for water removal, but are not useful in subject process, are ethylene glycol and diethylene glycol.

The advantages of the process invention are found to be in the simplicity and modest scale of the apparatus needed to run the process; the ease of renewing or replenishing solvent; the longevity of the apparatus due to the mild conditions of operation; and the low energy consumption, all in addition to the avoidance of atmospheric pollution and the economy of recycling the sterilizing gas mixture.

The invention is illustrated by the following examples. Percentages are by volume unless otherwise specified.

EXAMPLES 1 AND 2

An impure gas mixture coming directly from a sterilizer outlet is introduced into a system as described above and in the drawing.

This mixture contains 50 percent by volume ethylene oxide/dichlorodifluoromethane mixture in which the ratio of ethylene oxide to dichlorodifluoromethane is 0.37 part by volume of ethylene oxide per part by volume of dichlorodifluoromethane and 50 percent by volume water vapor and air in which the ratio of water vapor to air is 0.075 part by volume of water vapor per part by volume of air. The mixture is saturated with water vapor, is at a temperature of 27° C., and is at atmospheric pressure.

The procedures noted above are used to remove essentially all of the water vapor (all but about 200–350 ppm) and that portion of the ethylene oxide/dichlorodifluoromethane, which can be condensed out by virtue of its being present in the air above the saturation point.

The mixture initially used in subject process (run 1 of each example), then, contains 27 ($\pm 3$) percent by volume ethylene oxide/dichlorodifluoromethane mixture (referred to as $EO/CCl_2F_2$) and about 73 ($\pm 3$) percent by volume air (the ppm of water is discounted).

Columns 3 and 9 are made of carbon steel, are packed with ⅜ inch carbon steel raschig rings, and have 3 to 6 theoretical mass transfer units. The operating pressures in psia and temperatures in degrees Centigrade (°C.) for each example and the concentration of $EO/CCl_2F_2$ into column 3 in percent by volume (balance air); the concentration of $EO/CCl_2F_2$ in the vent line 7 in percent by volume (balance air); the gas flow rate in SCFH; the solvent flux rate in gallons per hour (GPH); and the part of solute ($EO/CCl_2F_2$) per part of solvent in column 3 (by weight) are given in the table below. There is a slight nitrogen feed to column 9 in both examples. The solvent used is diethylene glycol monobutyl ether.

| Ex. | temp. in column 3 (°C.) | pressure in column 3 (psia) | temp. in column 9 (°C.) top | temp. in column 9 (°C.) bottom | pressure in column 9 (psia) | run | gas flow rate (SCFH) | solvent flow rate (GPH) | $EO/CCl_2F_2$ into column 3 (percent) | $EO/CCl_2F_2$ in vent air (percent) | part of $EO/CCl_2F_2$ per part of solvent in column 3 (by weight) |
|---|---|---|---|---|---|---|---|---|---|---|---|
| 1 | 4.5 | 195 | 4.5 | 104 | 15 | 1 | 90 | 15 | 27 | 0.17 | 0.05 |
|   |   |   |   |   |   | 2 | 116 | 15 | 20 | 0.24 | 0.05 |
|   |   |   |   |   |   | 3 | 120 | 15 | 10 | 0.15 | 0.025 |
|   |   |   |   |   |   | 4 | 90 | 15 | 5 | 0.05 | 0.01 |

-continued

| Ex. | temp. in column 3 (°C.) | pressure in column 3 (psia) | temp. in column 9 (°C.) | | pressure in column 9 (psia) | run | gas flow rate (SCFH) | solvent flow rate (GPH) | EO/CCl$_2$F$_2$ into column 3 (percent) | EO/CCl$_2$F$_2$ in vent air (percent) | part of EO/CCl$_2$F$_2$ per part of solvent in column 3 (by weight) |
|---|---|---|---|---|---|---|---|---|---|---|---|
| | | | top | bottom | | | | | | | |
| 2 | 4.5 | 120 | 4.5 | 104 | 15 | 1 | 150 | 15 | 29.6 | 1.8 | 0.1 |
| | | | | | | 2 | 150 | 15 | 11.9 | 0.85 | 0.036 |
| | | | | | | 3 | 150 | 15 | 5.3 | 0.55 | 0.015 |

It is found that essentially all of the EO/CCl$_2$F$_2$ absorbed in column 3 is desorbed in column 9 and recovered.

I claim:

1. A process for the separation of a second mixture consisting essentially of ethylene oxide and dichlorodifluoromethane from a first mixture comprising ethylene oxide, dichlorodifluoromethane, and air comprising passing the first mixture through two zones connected in series, in a closed system, according to the following steps:

(a) passing the first mixture, in gaseous form, into an absorption zone and contacting said first mixture therein counter-currently with an organic liquid solvent, which has a boiling point of at least 120° C. and is capable of absorbing ethylene oxide and dichlorodifluoromethane under process conditions, at a pressure of about 80 psia to about 450 psia and a temperature of about minus 12° C. to about 24° C., the solvent being present in sufficient amount to absorb essentially all of the ethylene oxide and dichlorodifluoromethane whereby liquid bottoms are formed, and the air, in gaseous form, passes overhead;

(b) passing the bottoms from step (a) into a desorption zone wherein the pressure is in the range of about 5 psia to about 25 psia, and the temperature is in the range of about minus 12° C. to about 24° C. at the top of the zone and in the range of about 40° C. to about 120° C. at the bottom of the zone with a temperature gradient in between, in such a manner that the ethylene oxide and dichlorodifluoromethane are vaporized forming a gaseous overhead and the solvent forms liquid bottoms; and (c) recovering the overhead from step (b).

2. The process defined in claim 1 wherein the first mixture as introduced into step (a) is comprised of about 2.5 to about 28 percent by volume of ethylene oxide, about 6.5 to about 68 percent by volume dichlorodifluoromethane, and about 8.5 to about 88 percent by volume air, the percent by volume being based on the total volume of said first mixture.

3. The process defined in claim 2 wherein the temperature in the absorption zone is about 0° C. to about 5° C.; the pressure in the absorption zone is about 120 psia to about 360 psia; the temperature in the desorption zone is about 0° C. to about 5° C. at the top and about 95° C. to about 105° C. at the bottom; and the pressure in the desorption zone is about 15 psia to about 20 psia.

* * * * *